(12) United States Patent
Valenzuela

(10) Patent No.: US 10,771,878 B2
(45) Date of Patent: *Sep. 8, 2020

(54) MINIATURE FORM FACTOR BLUETOOTH DEVICE

(71) Applicant: Acouva, Inc., San Francisco, CA (US)

(72) Inventor: Victor Manuel Valenzuela, Hayward, CA (US)

(73) Assignee: Acouva, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/559,070

(22) Filed: Sep. 3, 2019

(65) Prior Publication Data

US 2019/0394552 A1 Dec. 26, 2019

Related U.S. Application Data

(63) Continuation-in-part of application No. PCT/US2019/026423, filed on Apr. 9, 2019, which is a continuation of application No. 15/950,110, filed on Apr. 10, 2018, now Pat. No. 10,219,063.

(51) Int. Cl.
- *H04R 1/10* (2006.01)
- *H04R 1/22* (2006.01)
- *H04R 1/08* (2006.01)

(52) U.S. Cl.
CPC .......... *H04R 1/1016* (2013.01); *H04R 1/222* (2013.01); *H04R 1/083* (2013.01); *H04R 1/1033* (2013.01); *H04R 2201/107* (2013.01); *H04R 2420/07* (2013.01); *H04R 2460/13* (2013.01)

(58) Field of Classification Search
CPC .. H04R 1/1016; H04R 1/222; H04R 2420/07; H04R 1/083

See application file for complete search history.

(56) References Cited

U.S. PATENT DOCUMENTS

| | | | |
|---|---|---|---|
| 8,855,345 B2 * | 10/2014 | Shennib | H04R 25/602 381/322 |
| 2008/0025358 A1 | 10/2008 | Goldstein et al. | |
| 2008/0253583 A1 * | 10/2008 | Goldstein | H04R 29/00 381/92 |
| 2009/0001045 A1 | 1/2009 | Goldstein et al. | |
| 2009/0010456 A1 * | 1/2009 | Goldstein | G10L 21/0264 381/110 |
| 2009/0007420 A1 | 3/2009 | Zhang | |
| 2009/0074201 A1 * | 3/2009 | Zhang | H04R 25/407 381/92 |
| 2015/0038212 A1 | 12/2015 | Baskaran et al. | |
| 2017/0023075 A1 | 8/2017 | Dohmen et al. | |
| 2017/0230752 A1 * | 8/2017 | Dohmen | H04R 1/1091 |
| 2017/0034734 A1 | 11/2017 | Masaki et al. | |
| 2017/0347348 A1 * | 11/2017 | Masaki | H04W 72/0406 |

\* cited by examiner

*Primary Examiner* — Tuan D Nguyen
(74) *Attorney, Agent, or Firm* — Growth IP

(57) ABSTRACT

Embodiments (e.g., of the system, etc.) can include a wireless in-ear utility device (e.g., miniature form factor Bluetooth device) with improved form factor in order to fit the small to extra small ear concha bowls and inner ear canals of one or more users. In embodiments, the improved wireless in-ear utility device can include tri-ear buds to be closer the users eardrum for higher sound quality performance and comfort in the user's ear when then in-ear utility device is worn, and allows for a higher level of comfort.

20 Claims, 7 Drawing Sheets

MINIATURE FORM FACTOR BLUETOOTH DEVICE

CROSS-REFERENCE TO RELATED APPLICATIONS

The present application is a continuation-in-part of and claims priority to PCT Patent Application No. PCT/US19/26423 filed 9 Apr. 2019, which claims priority to U.S. patent application Ser. No. 15/950,110, filed 10 Apr. 2018, each of which are incorporated in their entirety herein by this reference.

TECHNICAL FIELD

The disclosure generally relates to one or more in-ear wireless devices designed for fitting smaller ears.

BACKGROUND

The following background description includes information that may be useful in understanding context in relation to embodiments described herein. The background description is not an admission that any of the information provided herein is prior art or relevant to the embodiments, or that any publication specifically or implicitly referenced is prior art.

With the development of portable multimedia devices and smart phones, many types of in-ear pieces—such as earphones and headsets—have been developed. However, conventional ear-tips/domes can traditionally be bulky and uncomfortable as well as limited in their technological abilities. For example, in order to get them to fit properly, they have to be trimmed to fit properly; this is time consuming and costly.

Therefore, a need exists for improvement and advancements, such as in relation to form factors and/or associated features.

Therefore, a need exists for more advanced in-ear wireless devices that can facilitate the comfort of wearing, especially in comparison with devices that can cause extreme discomfort and may cause damage to the ear concha bowl and inner ear canals, causing pressure and extreme discomfort.

BRIEF DESCRIPTION OF THE FIGURES

Figures provided herein may or may not be provided to scale. The relative dimensions or proportions may vary. Embodiments can be sized to fit within an extra small to large ear canal of a user.

FIG. 1 illustrates an example of a wireless in-ear utility device 101 configured to provide retention by allowing 102,103,104 to compress from 10% to 15% independently in ear canal 106, therefore retaining the device in the user's ears without discomfort, according to an embodiment of the technology.

FIG. 2 illustrates an example of an embodiment of the technology in which a Tri-comfort Tips outer circumference of the Tri-comfort Tips 201 has been designed to accommodate an oval outer shape that mimics the ear canal that attaches to a wireless in-ear utility device 102, such as the in-ear main trunk support 203 shown on the solid device shown in FIG. 2, and where the insert horn 202 is designed to allow for the Tri-comfort Tips to snap on and increase amplification, and where the insert horn is permanently attached to 203, according to an embodiment of the technology.

FIG. 7 additionally illustrates a variation of a wireless in-ear utility device 702 designed to fit in the user's ear canal, where the main trunk support 703 goes deeper into the ear canal, therefore allowing for better sound quality enhancement performance with less power, being that the output of the sound port is closer to the eardrum, according to an embodiment of the technology.

DESCRIPTION OF EMBODIMENTS

Figure 1:
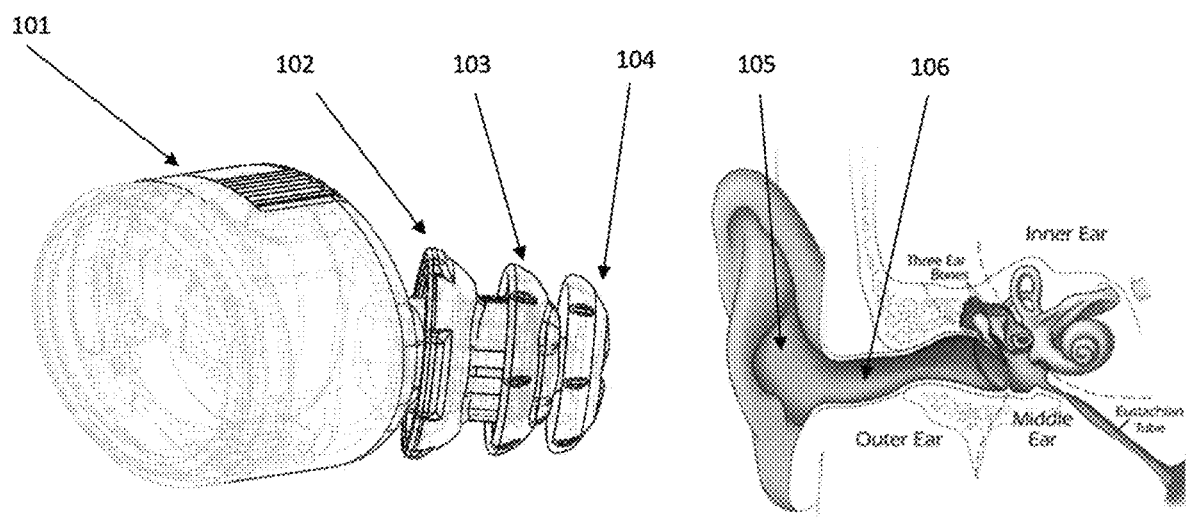
FIG. 1 illustrates an example of a wireless in-ear utility device 102 including a solid device sized to fit a concha bowl 105 and an inner ear canal 106, according to an embodiment of the technology.
Figure 2:
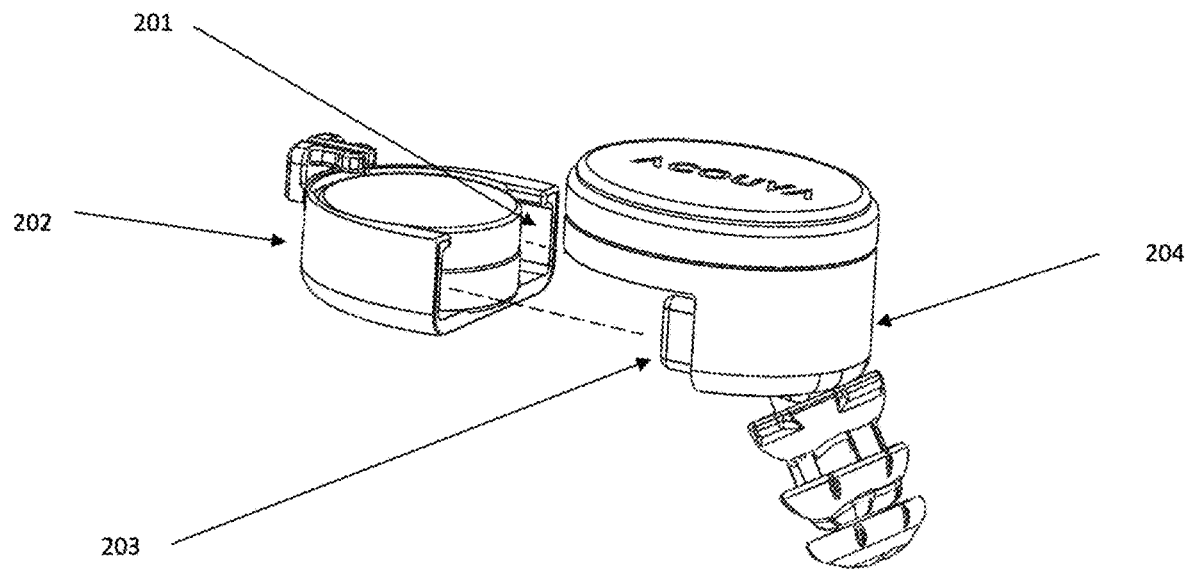
FIG. 2 illustrates an example of a wireless in-ear utility device 204, battery main trunk support 203 shown with solid main trunk support, where the wireless in-ear utility device 204 is designed to allow for a modular battery 202 to snap on to 204 with 1 Lbs to 2 Lbs of force (and/or any suitable force), to lock into 201 cavity, according to an embodiment of the technology.
Figure 3:
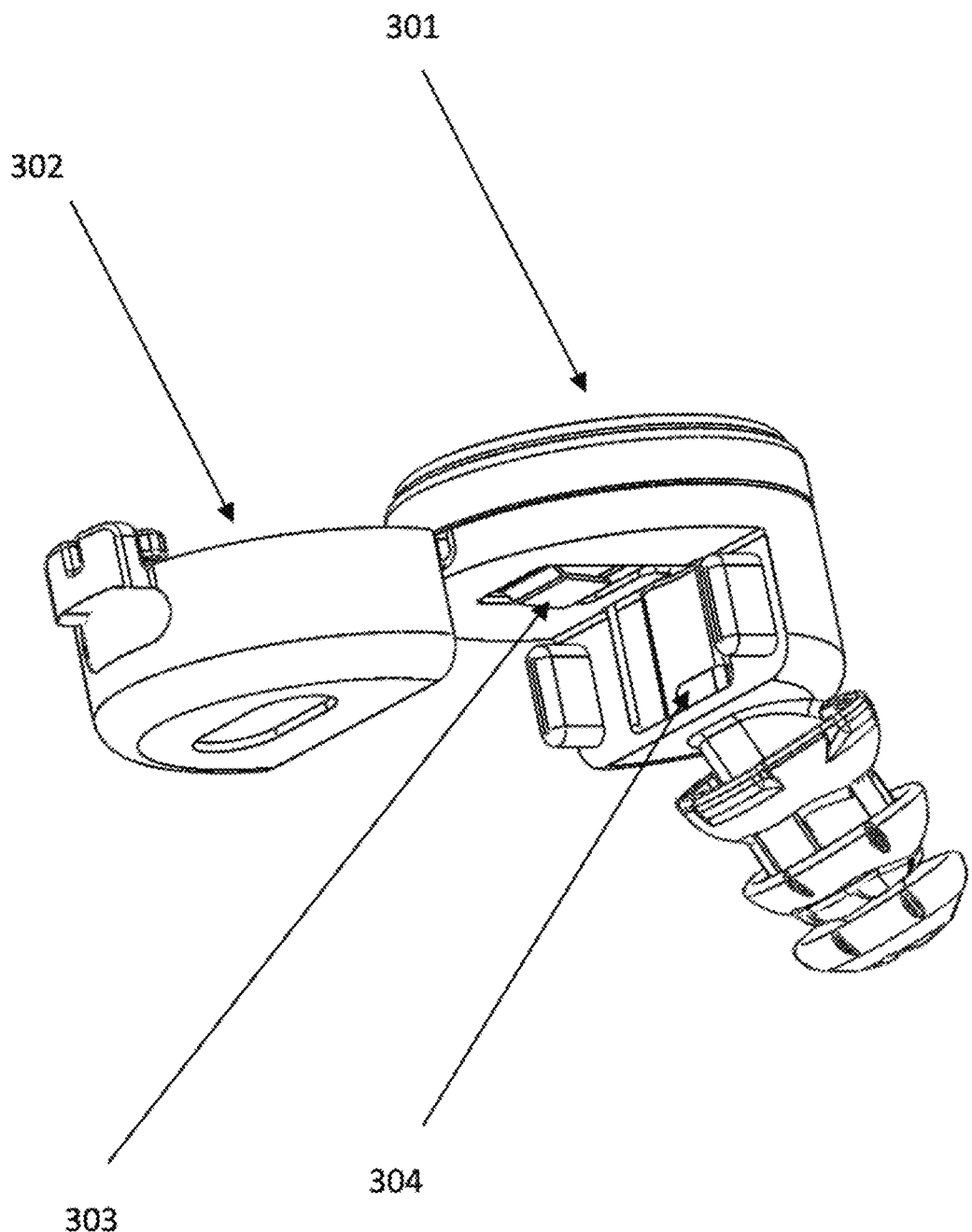
FIG. 3 illustrates an example of a wireless in-ear utility device 301 which is inserted into a small ear of the concha bowl and inner ear canal (e.g., concha bowl 105, inner ear canal 106, etc.) and allowing the wireless in-ear utility device 301 to have two contacts 303 and 304 to transfer power from the modular battery 302 to wireless in-ear utility device 301, according to an embodiment of the technology.
Figure 4:
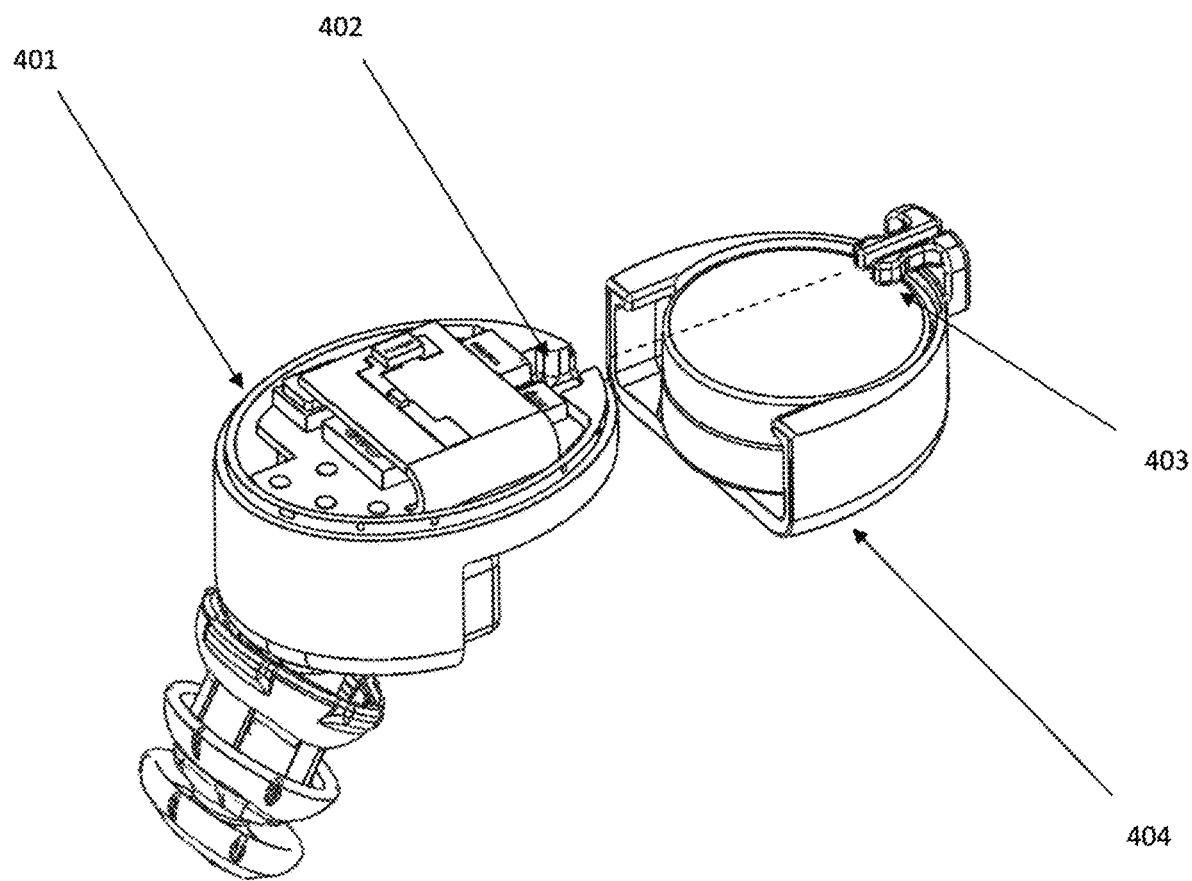
FIG. 4 illustrates an example of wireless in-ear utility device 401 and modular battery 404 has a third locking feature 403 that engages into the cavity of 402, according to an embodiment of the technology.
Figure 5:
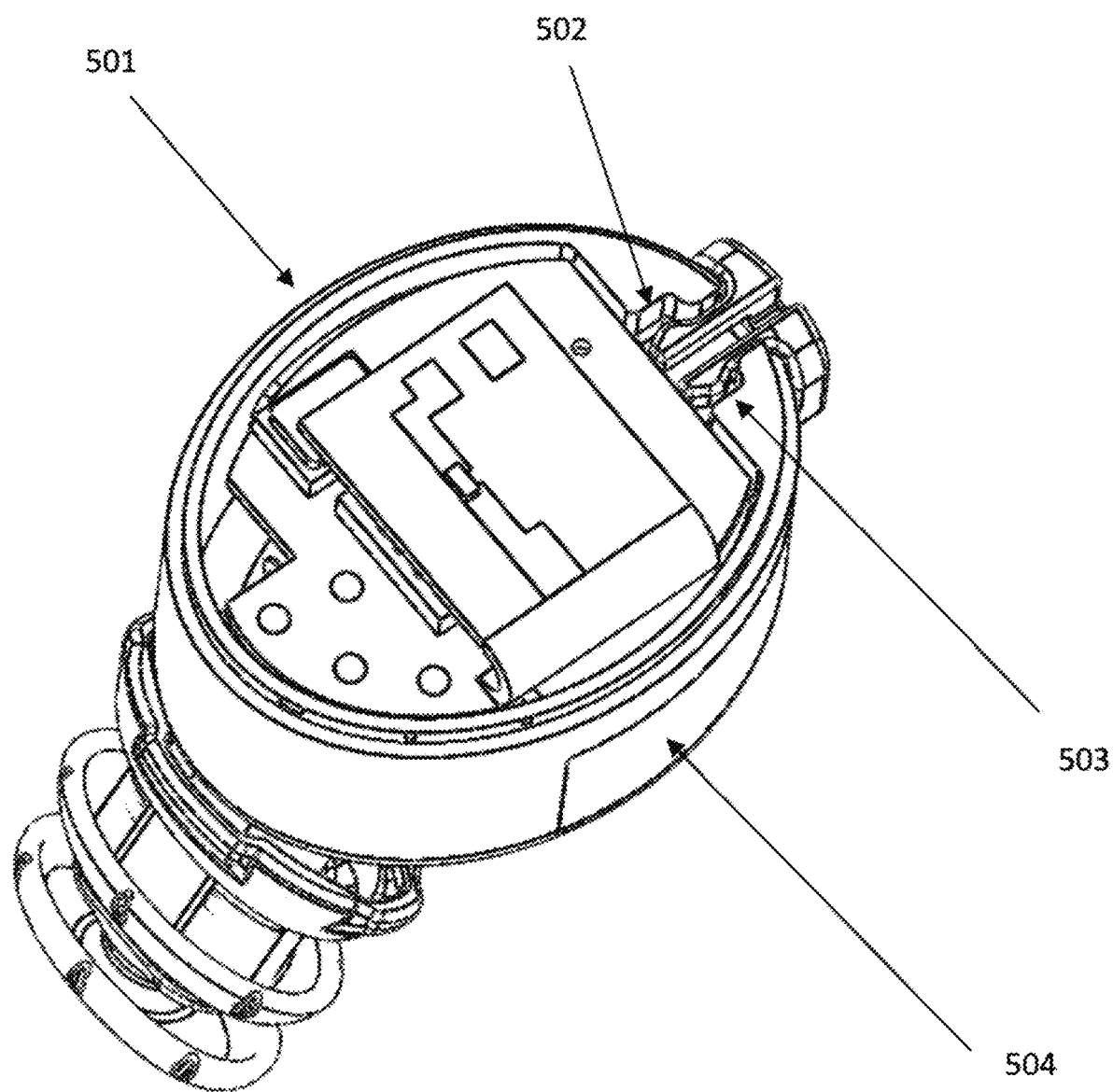
FIG. 5 illustrates an example of a wireless in-ear utility device 501 and the cavity 502 with the third locking feature 503 engaged, and requiring 2 lbs to 3 lbs (and/or any suitable force) to remove 504 from wireless in-ear utility device 501, where this is a safety feature, so that modular battery 504 will not fallout into the user's concha bowl and inner ear canal (e.g., concha bowl 105, inner ear canal 106, etc.), according to an embodiment of the technology.
Figure 6:
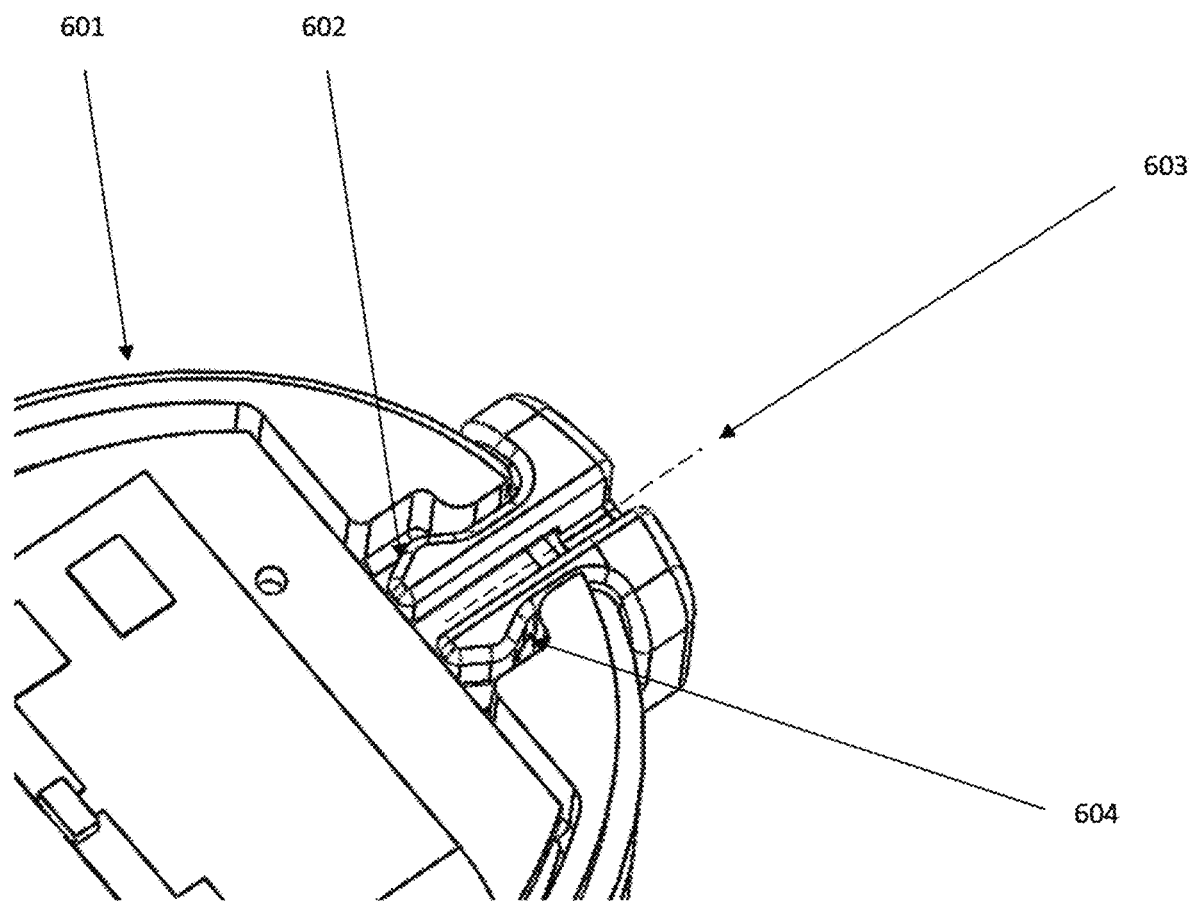
FIG. 6 illustrates an example of a wireless in-ear utility device 601 and the locking feature 602 and 604, where third locking feature 603 can include a canal that allows for sound to enter into the microphone and this canal feature can also allow for 602 and 604 to clap to snap in with 1 lbs to 2 lbs (and/or any suitable force) and to snap out with a force of 2 lbs to 3 lbs (and/or any suitable force) to remove from wireless in-ear utility device 601, according to an embodiment of the technology.

The following description of the embodiments (e.g., including variations of embodiments, examples of embodiments, specific examples of embodiments, other suitable variants, etc.) is not intended to be limited to these embodiments, but rather to enable any person skilled in the art to make and use.

Embodiments (e.g., of the system, etc.) can include a wireless in-ear utility device (e.g., miniature form factor Bluetooth device) with improved form factor in order to fit the small to extra small ear concha bowls and inner ear canals of one or more users. In embodiments, the improved wireless in-ear utility device can include tri-ear buds to be closer the users eardrum for higher sound quality performance and comfort in the user's ear when then in-ear utility device is worn, and allows for a higher level of comfort.

In embodiments, the improved wireless in-ear utility device can additionally or alternatively include a separate battery module attachment that allows for minimum user downtime by swapping out the batteries (e.g., used batteries) for fully charged ones. In specific examples, such functionality can be suited for users who rely on the wireless in-ear utility device as part of their daily life, as it can be useful to have wireless in-ear utility device(s) that can be up and ready within 30 to 40 seconds (e.g., minimal downtime, etc.).

Embodiments of the wireless in-ear utility device can be used for a variety of purposes and can additionally include a variety of electronic packages, such as for use as a Psap, hearing aids, for use as a music player, headphone device, for use in various external health-monitoring applications accessories, and/or for any suitable application requiring and/or usable with an improved wireless in-ear utility device. Embodiments can provide a wireless in-ear utility device configured to have a variety of electronic packages. The electronic packages may serve a variety of functions, such as a Bluetooth device, noise cancellation device that allows the user to focus on sounds of interest, a health-awareness monitoring and safety awareness monitoring device, fitness device, such as where embodiments or internal accessories devices can include the sensors and electronic configuration needed to carry out its mission in configuration with wireless in-ear utility device. In specific examples, the one or more swappable battery modules can allow for an improved wireless in-ear utility device (e.g., improvements over having to be recharged in a charger for multiple hours such as in traditional in-ear devices, etc.), where the improved wireless in-ear utility device with a swappable battery module can include a 30 to 40 seconds downtime, or a downtime of a shorter time period (and/or of any suitable downtime).

In embodiments, the swappable batteries can confer improvements to the wireless in-ear utility device (e.g., where the traditional in-ear devices such as in-ear buds may require to be put in a charger case and allow to charge for 2 or more hours, before the user can use the in-ear buds; where traditional in-ear devices may not be designed to be worn for extended periods of time, etc.). In specific examples, the wireless in-ear utility device has been designed to be worn for extended periods of time.

Embodiments can function to provide one or more wireless in-ear utility devices designed specifically to fit smaller ears. Embodiments can additionally or alternatively function to provide one or more wireless in-ear utility devices configured to provide a high level of in-ear, longer lasting comfort, such as with users that have smaller concha bowl and/or inner ear canals, and/or such as with users who use the wireless in-ear utility device for more than 6-12 hours a day. In specific examples, embodiments can enhance users' day to day business, such as users with high usage of phones or using as a hearing assistant and as a hearing aid.

In specific examples, the wireless in-ear utility device (e.g., miniature form factor Bluetooth device) can be designed for in-ear comfort, to provide longer lasting comfort for all day usage. In specific examples, the wireless in-ear utility device (e.g., miniature form factor Bluetooth device) includes (e.g., includes components providing functionality of, etc.) multiple communication, two way communication, streaming audio, phone calls, Bluetooth (and/or other wireless) network communications with other devices, language and translation to the owner language for a two way communication in any language, Frequencies to enhance hearing lost, Long-range wireless network including a multimedia communications network, Communication Architecture Monitoring exterior Key Biometrics, Communication Architecture Safety Awareness, and/or other suitable functionality.

The distance of the in-ear utility device 702 to a given user's ear canal varies based on the depth of the user's ear canal. Some users have shallow ear canals while other users have deep ear canals. Therefore, the distance of the in-ear utility device iota may vary in depth from user to user, but can be configured to reside at any suitable depth in relation to the ear canal and/or other suitable regions of the ear. Therefore, in specific examples, the one or more components of the in-ear utility device 702 can be designed to keep at a great depth (e.g., pre-determined; a depth to avoid harm and/or discomfort, etc.) and away from a user eardrum.

In specific examples, the distal end (e.g., the outer end of the solid device 702, of the in-ear utility device 102) can reside just outside the user's ear so that the in-ear utility device 702 may be easily removed by hand. In some embodiments, the in-ear utility device 703 might reside inside the ear canal with no part of the device outside the ear, but such embodiments can still be inserted into the ear canal as for the tri-ear buds and easily removed by a hand.

In examples, the miniature (e.g., smaller, etc.) form factor in-ear utility device 702 rests into the user's concha bowl of the user's ear more so than a typical Bluetooth device. Thus, in specific examples, the specific components in the electronic component package may need to be carefully selected and packaged into a smaller form factor size, in addition to other characteristics to prevent harmonic distortion and feedback noise between the mic and speaker chamber, which are designed to be isolated from each other.

In specific examples, the in-ear utility device 702 is inserted into a user's ear canal without damaging the in-ear utility device 702 or causing harm to the user's ear. In specific examples, the conformability to the user's ear canal tri-ear buds 703 cushions the user's ear canal from causing any discomfort. However, the in-ear utility device 702 and/or suitable components can be sized and/or otherwise configured in any suitable manner for reducing discomfort and/or harm.

Embodiments of the in-ear utility device 702 are preferably wearable for long periods of time (e.g., at least 6-12 hours continuously, or throughout a day, etc.). In specific examples, the tri-ear buds need to be comfortable for the user in order for the user to be able to wear the in-ear utility device 702 for long periods of time. In specific examples, comfort from the tri-ear buds are designed to work in conjunction with any in-ear utility device/hearing aids/psap/ for long periods without causing any discomfort.

Studies show that typical human ear canals are very sensitive. Thus, embodiments of the in-ear utility device 702 can cover a fairly wide range of ear canal sizes. In specific examples, the in-ear utility device 702 was designed for extra small ears. For example, in-ear utility device 702 takes into account for variations in size of user's ear canals (e.g., extra small, small, and medium, large and extra large). For example, the in-era utility device 702 can possess a shape, form-factor, a material construction, and/or other suitable characteristics that can account for variations in size of user's ear canals (e.g., extra small, small, medium, large and extra-large). In variations, different variants of the tri-ear buds can be constructed to account for physical differences in user's ear regions.

Any number of tasks may be performed by the in-ear utility device 702, according to an embodiment of the invention. The wireless in-ear utility device 702 and the solid device portion may include a variety of in-ear devices, such as hearing aids and wearable devices. In embodiments, the device electronics preferably reside in the solid device and not in the tri-ear buds 703, but can additionally or alternatively reside in and/or in relation to any suitable components. In embodiments, the wireless in-ear utility device 702 and/or any suitable components can include any suitable characteristics and/or components described in U.S. patent application Ser. No. 15/950,110, filed 10 Apr. 2018, which is herein incorporated by reference in its entirety. In specific examples, the wireless in-ear utility device can include any suitable characteristics described in relation to the wireless in-ear utility device described in U.S. patent application Ser. No. 15/950,110, filed 10 Apr. 2018.

Embodiments of the wireless in-ear utility device 702 are preferably designed for a user placing the wireless in-ear utility device 702 into small ear canals. Embodiments of the wireless in-ear utility device 702 preferably Allows a battery module 701 to snap on and off the device housing, e.g., the solid device 702 shown in FIG. 7, where a specific example of the battery module 701 is shown in FIG. 7.

Figure 7:
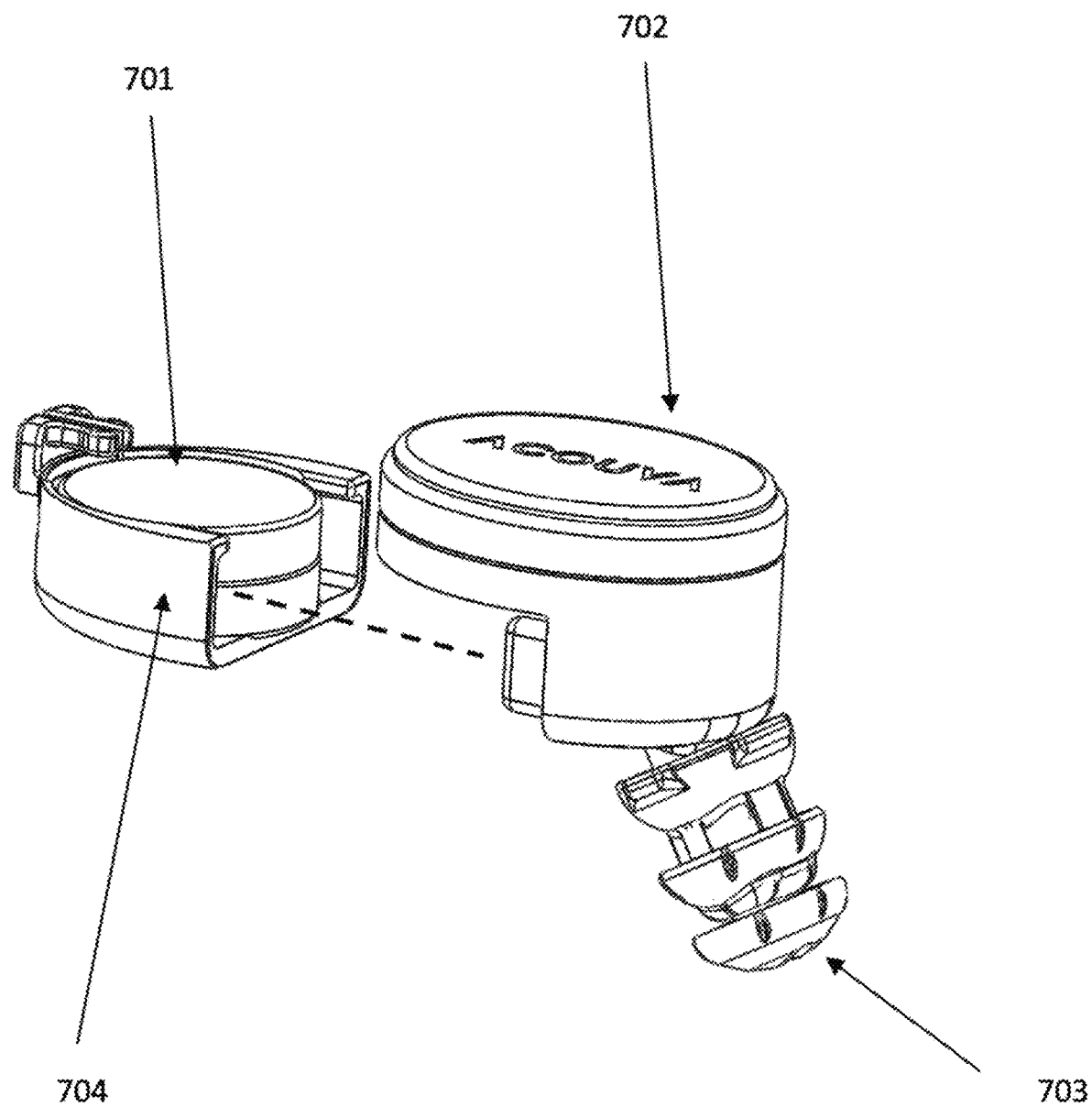
FIG. 7 illustrates a variation of a wireless in-ear utility device 702 configured as a multi, integrated body (e.g., rather than as one single-pieced body, etc.), where example 701 is detachable to allow the user to swap out the battery to minimize user downtime, where the battery is molded in a battery housing, which allows for the battery to be installed in only one way, preventing the user from installing the battery incorrectly and causing a short or device failure; where the battery (e.g., a lithium ion rechargeable battery, etc.) is then placed into a charger case and swapped out with a fresh one with minimum user downtime, according to an embodiment of the technology.

FIG. 7 illustrates an example of wireless in-ear utility device 701 in which a battery module can snap on and off the solid device portion 702, according to an embodiment of the technology. As shown in FIG. 7, in a specific example, the plastic battery module 701 lithium ion batteries is bonded to the battery housing 704 using only medical grade epoxy, according to an embodiment of the technology.

In specific examples, the degree of inclination of the tri-ear buds 703 in comparison is inclined approximately 2 degrees step allowing for ease of insertion of the wireless in-ear utility device 701, according to an embodiment of the technology. However, the relative incline can be at any suitable degrees.

Figure 8:
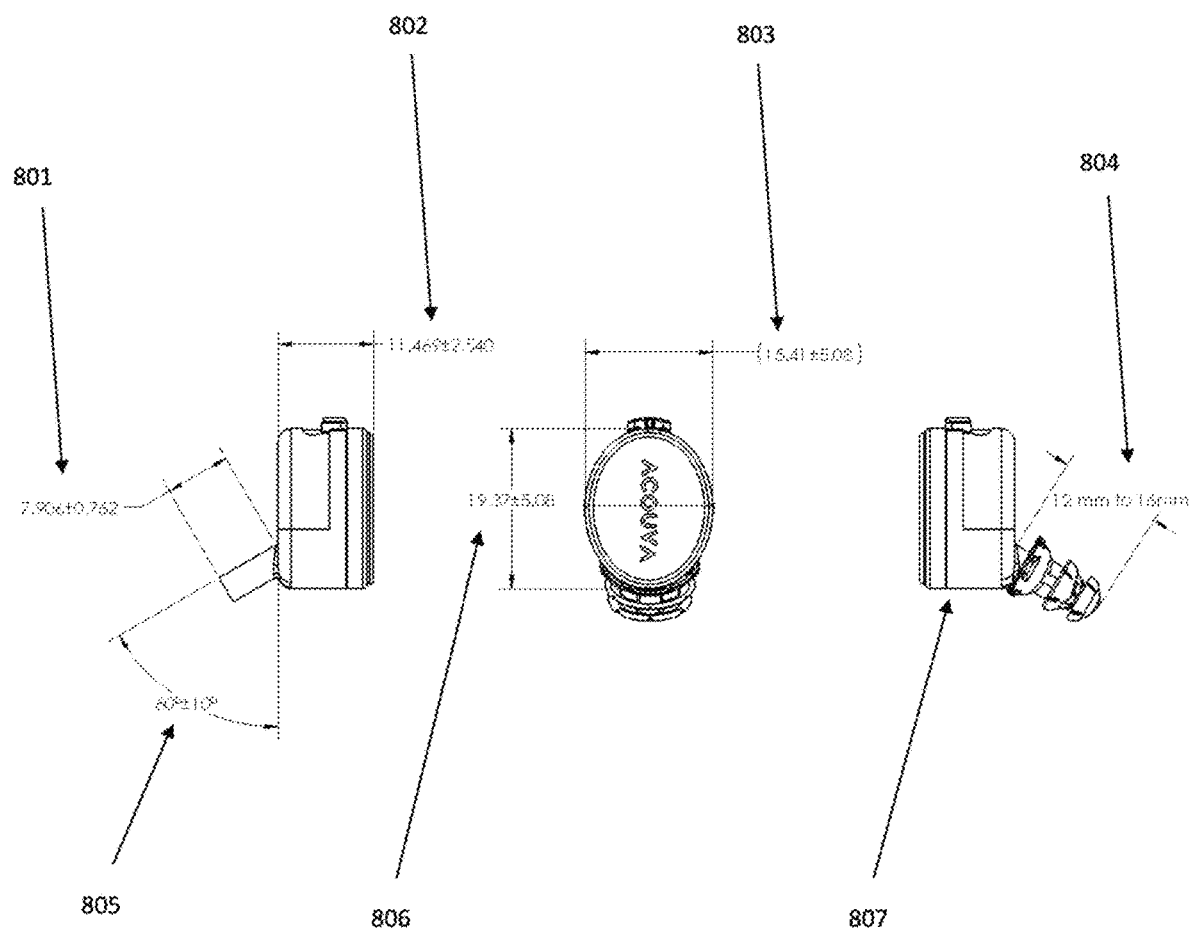
FIG. 8 illustrates an example of a wireless in-ear utility device 807 in which the dimensions shown 801, 802, 803, 804, 805 and 806 each have their own tolerance; and within the range, all the internal components have been packaged into, and not to exceed outside of these parameters, in order to maintain extreme comfort within a small ear concha bowl and ear canal, according to an embodiment of the technology.

FIG. 8 illustrates specific examples of a wireless in-ear utility device 807 in which the dimensions shown 801, 802, 803, 804, 805 and 806 each have their own tolerance; and within the range, all the internal components have been packaged into, and not to exceed outside of these parameters, in order to maintain extreme comfort within a small ear concha bowl and ear canal, according to an embodiment of the technology. However, any suitable components in FIG. 8 can have any suitable parameters, such as any suitable parameters designed to fit a user's small ear concha bowl and ear canal (e.g., small relative an average human; small relative a user with comparable demographic, genetic, and/or other suitable characteristics; etc.).

However, the wireless in-ear utility device (e.g., miniature form factor Bluetooth device, etc.) can be configured in any suitable manner.

The wireless in-ear utility device preferably includes Bluetooth wireless functionality, but can additionally or alternatively be used with any suitable communication protocols, including one or more of: WiFi, radiofrequency, Zigbee, Z-wave, wired communication, and/or any suitable types of communication.

Embodiments of the technology provide a Bluetooth in-ear utility device comprising a housing with an oval shape trunk to fit into a user's ear canal within the first bend of the ear canal, the housing having a proximal end configured to reside in the user's ear canal (e.g., at a distance no more than 12 to 16 millimeters from the entrance of the user's ear canal). A bone conduction microphone configured to detect resident frequencies to facilitate user voice recognition.

Various embodiments of the technology have been described in detail with reference to the accompanying drawings. References made to particular examples and implementations are for illustrative purposes, and are not intended to limit the scope of the technology or the claims.

It should be apparent to those skilled in the art that many more modifications of the in-ear utility device besides those already described are possible without departing from the inventive concepts herein. The inventive subject matter, therefore, is not to be restricted except by the scope of the appended claims. Moreover, in interpreting both the specification and the claims, all terms should be interpreted in the broadest possible manner consistent with the context.

Headings and sub-headings provided herein have been provided as assistance to the reader and are not meant to limit the scope of the technology disclosed herein. Headings and sub-headings are not intended to be the sole or exclusive location for the discussion of a particular topic.

While specific embodiments of the technology have been illustrated and described, it will be clear that the technology is not limited to these embodiments only. Embodiments of the technology discussed herein may have generally implied the use of materials from certain named equipment manufacturers; however, the technology may be adapted for use with equipment from other sources and manufacturers. Equipment used in conjunction with the technology may be configured to operate according to conventional protocols (e.g., Bluetooth, Wi-Fi) and/or may be configured to operate according to specialized protocols. Numerous modifications, changes, variations, substitutions and equivalents will be apparent to those skilled in the art without departing from the spirit and scope of the technology as described in the claims. In general, in the following claims, the terms used should not be construed to limit the technology to the specific embodiments disclosed in the specification, but should be construed to include all variants that operate under the claims set forth herein below. Thus, it is intended that the technology covers the modifications and variations of this technology provided they come within the scope of the appended claims and their equivalents.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As used herein, and unless the context dictates otherwise, the terms "ambient noise" and "ambient sound" have been used synonymously. Similarly, "sound" and "noise" have been used synonymous, except where the context shows a difference in meaning, e.g., "meaningful sound from mere noise."

The channel frequency filters can be calibrated and tuned in prior to shipping in high volume.

Any of the variants described herein (e.g., embodiments, variations, examples, specific examples, figures, etc.) and/or any portion of the variants described herein can be additionally or alternatively combined, aggregated, excluded, used, and/or otherwise applied.

Embodiments of the method and/or systems can include every combination and permutation of the various system components and the various method processes, including any variants (e.g., embodiments, variations, examples, specific examples, figures, etc.), where portions of embodiments of the method and/or processes described herein can be performed asynchronously (e.g., sequentially), concurrently (e.g., in parallel), or in any other suitable order by and/or using one or more instances, elements, components of, and/or other aspects of the systems and/or other entities described herein.

As a person skilled in the art will recognize from the previous detailed description and from the figures and claims, modifications and changes can be made to embodiments of the methods, systems, and/or variants without departing from the scope defined in the claims. Variants described herein not meant to be restrictive. Certain features included in the drawings may be exaggerated in size, and other features may be omitted for clarity and should not be restrictive. The figures are not necessarily to scale. The absolute or relative dimensions or proportions may vary. Section titles herein are used for organizational convenience and are not meant to be restrictive. The description of any variant is not necessarily limited to any section of this specification.

I claim:

1. A Bluetooth in-ear utility device with miniature form factor, comprising:
    a housing comprising an oval shaped trunk configured to reside in an ear canal of a user's ear within the first bend of the ear canal at a distance less than 16 millimeters from the entrance of the ear canal,
    wherein the housing is configured to reside in a concha bowl distal portion of the user's ear,
    wherein the oval shaped trunk is shaped to allow the oval shaped trunk to enter the ear canal while reducing interference with an ear canal wall;
    a speaker (receiver) port, wherein the oval shaped trunk is shaped to allow the oval shaped trunk to directly enter the ear canal wall while preventing the speaker port from being blocked by the ear canal wall; and
    a bone conduction microphone configured to detect resident frequencies to facilitate user voice recognition.

2. The Bluetooth in-ear utility device with miniature form factor of claim 1, further comprising a microphone port located a distal external surface of the housing and configured to reside in a user's ear Concha bowl to listen for ambient external sounds from the low/mid/high frequencies (20 Hz to 40,000 kHz).

3. The Bluetooth in-ear utility device with miniature form factor of claim 2, wherein the microphone port is further configured to listen for voice commands and approaching emergency vehicles.

4. The Bluetooth in-ear utility device with miniature form factor of claim 3, further comprising a processing system configured to improve signal-to-noise ratio based on the microphone port, wherein in response to detecting the approaching emergency vehicles approaching, the microphone port will process, frequencies from the low/mid/high frequencies (20 Hz to 40,000 kHz) through known frequencies generated and stored in internal memory of the processing system, wherein the emergency vehicles are heard from the microphone port and matched with the frequency stored in the internal memory, wherein the Bluetooth in-ear utility device is configured to notify a user that there is an emergency vehicle approaching and to take caution.

5. The Bluetooth in-ear utility device with miniature form factor of claim 2, wherein the microphone port is configured to listen for ambient external sounds from the low/mid/high frequencies (20 Hz to 40,000 kHz) for calibration to a user's voice, wherein the calibrated distance from a mouth and the user's ear is constant for enabling the microphone port to detect and facilitate user voice recognition for calibration specific to the user's voice based on Artificial intelligence prior to transmitting the first ambient external sounds to a digital signal processor of the Bluetooth-in ear utility device, wherein second ambient external sounds from a second Bluetooth in-ear utility device have undergone digital signal processing before transmission to the Bluetooth in-ear utility device, wherein a processing system of the Bluetooth in-ear utility device is configured apply enhanced ambient external sound and data from an enhanced second Mic in recognizing speech frequencies from the low/mid/high (20 Hz to 40,000 kHz) speech frequencies through the processing system, for facilitating the user voice recognition.

6. The Bluetooth in-ear utility device with miniature form factor of claim 1, wherein the Bluetooth in-ear utility device is configured to be worn in the user's ear or a user's second ear or either ear of a given user, wherein the Bluetooth in-ear utility device is perfectly symmetrical for residing in a right ear or left ear of the given user.

7. The Bluetooth in-ear utility device with miniature form factor of claim 1, further comprising an acoustic speaker chamber located within the housing, wherein a processing system of the Bluetooth in-ear utility device is configured to send a digital decoded signal through the acoustic speaker chamber that is designed to eliminate resident frequency, therefore reducing or eliminating harmonic distortion.

8. The Bluetooth in-ear utility device with miniature form factor of claim 1, further comprising an external microphone and a Bone conduction microphone usable in conjunction with a processing system of the Bluetooth in-ear utility device for improving signal-to-noise ratio associated with external sounds, wherein noise comprising wind and low/mid/high 20 Hz to 40,000 kHz frequencies are cancelled out, wherein the Bone conduction microphone is configured to filter out unwanted frequencies by picking up the resident frequency first and the external Microphone picking up ambient frequency.

9. The Bluetooth in-ear utility device with miniature form factor of claim 1, further comprising a speaker associated with the speaker port, wherein the speaker is located near a distal end of the oval shaped trunk and resides in the ear canal, and wherein the speaker is configured to play external sounds and to produce maximum sound output quality given a location near to an ear drum.

10. The Bluetooth in-ear utility device with miniature form factor of claim 1, further comprising an internal horn located in the oval shaped trunk and configured for sound amplification in relation to decrease of power gain of an electrical signal associated with an acoustic speaker chamber of the Bluetooth in-ear utility device with miniature form factor.

11. The Bluetooth in-ear utility device with miniature form factor of claim 1, wherein the Bluetooth in-ear utility device is configured for minimum downtime and comprises a swappable Lithium ion battery module that takes the user a minimum of 30 seconds to swap out with a fully charged Lithium ion battery module from a charger case.

12. The Bluetooth in-ear utility device with miniature form factor of claim 11, wherein the housing, the swappable Lithium ion battery module, and the fully charged Lithium ion battery module are shaped to prevent incorrect insertion into the Bluetooth in-ear utility device with miniature form factor.

13. The Bluetooth in-ear utility device with miniature form factor of claim 11, wherein the swappable Lithium ion battery module requires a snap in and out force from 2 to 3 Lbs in order to keep the battery module from falling out of the Bluetooth in-ear utility device.

14. The Bluetooth in-ear utility device with miniature form factor of claim 11, wherein the swappable Lithium ion battery module includes a port designed for allowing ambient sounds to enter into a microphone port of the Bluetooth in-ear utility device with miniature form factor.

15. The Bluetooth in-ear utility device with miniature form factor of claim 11, wherein the swappable Lithium ion battery module is insertable into a battery charger case, that allows for the swappable Lithium ion battery module to be inserted only one way for prevention from being inverted in the battery charger case or in the Bluetooth in-ear utility device, wherein the being inverted cause a short circuit and possible fire.

16. The Bluetooth in-ear utility device with miniature form factor of claim 11, wherein the Bluetooth in-ear utility device and the swappable Lithium ion battery module are designed with the miniature form factor for fitting into smaller ear.

17. The Bluetooth in-ear utility device with miniature form factor of claim 11, further comprising two battery contacts configured to apply spring force onto the swappable Lithium ion battery module and keeping it from falling out.

18. The Bluetooth in-ear utility device with miniature form factor of claim 11, comprising two battery main trunk supports for aligning with a cavity of the swappable Lithium ion battery module and for guiding insertion of the swappable Lithium ion battery module into the two battery main trunk support through rails support.

19. The Bluetooth in-ear utility device with miniature form factor of claim 1, wherein the oval shaped comprises a length not to exceed 12 mm, therefore configured to reside away from the first bend of the ear canal, and configured to keep the speaker port from getting blocked.

20. The Bluetooth in-ear utility device with miniature form factor of claim 1, further comprising an acoustic speaker chamber located within the housing, wherein a processing system of the Bluetooth in-ear utility device is configured to send Near-field magnetic induction (NFMI) digital decoded signal through the users head to the device in the opposite side and into the processor to decode and send the audio through the acoustic speaker chamber that is designed to eliminate resident frequency, therefore reducing or eliminating harmonic distortion.

* * * * *